(12) United States Patent
Setzer et al.

(10) Patent No.: US 11,612,886 B2
(45) Date of Patent: Mar. 28, 2023

(54) DISPENSER, SYSTEM AND METHOD FOR TAKING UP AND DISPENSING FLUID VOLUMES

(71) Applicant: BRAND GMBH + CO KG, Wertheim (DE)

(72) Inventors: Daniel Setzer, Schneeberg (DE); Jürgen Schraut, Rettersheim (DE)

(73) Assignee: BRAND GMBH + CO KG, Wertheim (DE)

( * ) Notice: Subject to any disclaimer, the term of this patent is extended or adjusted under 35 U.S.C. 154(b) by 792 days.

(21) Appl. No.: 16/486,883

(22) PCT Filed: Feb. 21, 2018

(86) PCT No.: PCT/EP2018/054289
§ 371 (c)(1),
(2) Date: Aug. 19, 2019

(87) PCT Pub. No.: WO2018/153924
PCT Pub. Date: Aug. 30, 2018

(65) Prior Publication Data
US 2020/0009546 A1 Jan. 9, 2020

(30) Foreign Application Priority Data
Feb. 23, 2017 (DE) .................... 20 2017 101 008.2

(51) Int. Cl.
*B01L 3/02* (2006.01)
(52) U.S. Cl.
CPC .......... *B01L 3/0227* (2013.01); *B01L 3/0234* (2013.01); *A61M 2205/3306* (2013.01);
(Continued)

(58) Field of Classification Search
None
See application file for complete search history.

(56) References Cited

U.S. PATENT DOCUMENTS

| 4,345,483 A | 8/1982 | Paletta et al. |
| 4,567,780 A | 2/1986 | Oppenlander et al. |

(Continued)

FOREIGN PATENT DOCUMENTS

DE 102013105495 A1 12/2014

*Primary Examiner* — Brian R Gordon
(74) *Attorney, Agent, or Firm* — David S. Safran; Calderon Safran & Cole P.C.

(57) ABSTRACT

A dispenser for taking up and discharging fluid volumes which has an exchangeable piston-cylinder unit. The dispenser has a housing and a device for incremental distance measurement that, when there is relative movement between the piston and the cylinder, the distance traveled by the piston relative to the housing can be determined incrementally. The dispenser has a piston actuation member which can be releasably connected to the piston moving the piston in order to take up and/or discharge fluid volumes. The dispenser has a position determining device which has a first position element and a second position element. The first position element is fixed in or on the housing of the dispenser. The second position element is coupled so as to be able to move with the piston actuation member. The position determining device is for continuously sensing the position of the second position element.

10 Claims, 3 Drawing Sheets

(52) U.S. Cl.
CPC ..... *B01L 2200/08* (2013.01); *B01L 2300/027* (2013.01); *B01L 2300/0627* (2013.01)

(56) References Cited

U.S. PATENT DOCUMENTS

| | | |
|---|---|---|
| 4,821,586 A | 4/1989 | Scordato et al. |
| 5,389,341 A | 2/1995 | Tuunanen et al. |
| 5,998,218 A | 12/1999 | Conley et al. |
| 6,428,750 B1 | 8/2002 | Rainin et al. |
| 2002/0025260 A1 | 2/2002 | Maruyama |
| 2010/0199789 A1 | 8/2010 | Magnussen et al. |
| 2018/0169647 A1* | 6/2018 | Reichmuth ........... B01L 3/0279 |

* cited by examiner

DISPENSER, SYSTEM AND METHOD FOR TAKING UP AND DISPENSING FLUID VOLUMES

BACKGROUND OF THE INVENTION

Field of the Invention

The invention relates to a dispenser for taking up and dispensing fluid volumes to which a piston-cylinder unit is releasably attachable, to a system for taking up and dispensing fluid volumes using such a dispenser and to a method for taking up and dispensing fluid volumes using such a dispenser.

Description of the Related Art

It is the object of systems of the type discussed to take up a fluid volume from a container and then to dispense it into one other or multiple other containers. Such systems serve, in particular, for the repeated dispensing, titrating or pipetting of liquids.

Such systems include a dispenser and a piston-cylinder unit which is realized as an exchangeable part and is releasably attachable to, in particular usable on or insertable in, the dispenser. After one or multiple dispensing operations, the piston-cylinder unit can be released from the dispenser. Another, in particular different, piston-cylinder unit can then be attached to the dispenser.

Such systems can be realized as manual or motor-driven handheld devices and precisely one piston-cylinder unit can be attached to the dispenser of said devices. There are also systems where a plurality of piston-cylinder units are attached at the same time to the dispenser of said systems, such as, for example, in the case of a pipetting machine.

Piston-cylinder units of the type discussed can be realized, for example, as displacement units with attachable pipettes or tips or as syringes. They each comprise a cylinder, in particular having a straight hollow cylinder with a substantially circular-ring-shaped cross section and an axial direction perpendicular thereto, and a piston which is displaceable in the cylinder in the axial direction thereof. As a result of displacing the piston, fluids can be taken up into the cylinder or into the tip attached therein and dispensed therefrom.

The piston cylinder units can be attachable to the dispenser by means of a movement which extends at least substantially in the axial direction of the dispenser. This allows for a simple, user-friendly, ergonomically advantageous and less error-prone operation of the corresponding system. In this case, the expression "axial direction of the dispenser" characterizes an alignment which matches with or is parallel to the longitudinal axis of the dispenser.

As an alternative to this, the piston-cylinder units can be attachable to the dispenser by means of a movement which extends at least substantially in the radial direction of the dispenser or sideways. In this case, the expression "radial direction of the dispenser" characterizes an alignment perpendicular to the axial direction of the dispenser.

A high degree of accuracy when taking up and dispensing fluid volumes is advantageous to the systems that are relevant here.

Precise measuring of the length of the displacement path of the piston of the piston-cylinder unit in the cylinder is essential to the accuracy or to the correctness and to the coefficients of variation when taking up or dispensing volumes with the systems of the type being discussed. The displacement of the piston in the cylinder is a substantially linear movement in the axial direction of the piston-cylinder unit.

European Patent EP 0 025 575 A1 and corresponding U.S. Pat. No. 4,345,483 A disclose a dosing device for smaller quantities of liquid within the millimeter and microliter range which comprises a piston-cylinder unit driven by a direct current motor, a housing, an optical digitally incremental distance measuring system, an optically digital measuring circuit and a control, compute and compare circuit. The distance measuring system has a transparent pulse rod which is provided with opaque markings and is fastened to the piston of the piston-cylinder system. The measuring circuit converts the stroke of the piston into a corresponding number of digital pulses.

In the case of the disclosed dosing device, the distance traveled by the piston relative to the housing of the dispenser when there is a relative movement between the piston and the cylinder can therefore be determined incrementally. In addition, the length of the displacement path of the piston in the cylinder is determined by counting the pulses and multiplying the counter reading with the distance between two adjacent bars of the grating (increment). In principle, therefore, the individual increments are added up here, proceeding from a starting point, the absolute position of which in the housing of the dosing device is unknown. Once the power supply has been switched on, the disclosed dosing device therefore only measures changes in relation to an unknown starting point (connection position).

In the prior art a microprocessor-controlled hand dispenser, the HandyStep® electronic, for dosing liquid volumes is disclosed in the general catalogue of the applicant (BRAND Complete Catalogue 900 (June 2013)). Here a syringe is insertable radially into the disclosed dispenser and the coded size thereof can be determined at a piston head of a piston of the syringe by means of light barriers. The piston head is coupled with a piston actuator. The stroke drive thereof is effected by an electric motor with worm gearing. The stroke is determined as a result of incremental rotary measuring at the electric motor and a reference point provided by a fixed switch. In the case of said dispenser also, the distance of the piston is only determined incrementally and indirectly at the electric motor. In addition, the light barriers are prone to faults.

SUMMARY OF THE INVENTION

The present invention focuses on piston-cylinder units which operate according to the principle of direct displacement and are suitable for the dispensing of liquids with high viscosity and/or high vapor pressure.

The present invention focuses on motor-operated, electronic multi-dispensers. In the case of such dispensers, the actuating of one key or multiple keys initiates a taking-up or drawing in or dispensing mechanism. The piston of a piston-cylinder unit attached to the dispenser is moved by means of a motor and the volume take-up and/or volume dispense is controlled by a microprocessor. The piston wipes the inside wall of the cylinder of the piston-cylinder unit in a sealing manner so that precisely reproducible volume results are obtained.

An object of the present invention is to improve a dosing device or the associated system or the corresponding method with regard to operational readiness, the handling of the piston-cylinder unit and/or the accuracy when taking up and dispensing fluid volumes.

According to a first aspect of the invention, the previously depicted object set is achieved by the dispenser as disclosed herein.

It goes without saying that designs, embodiments, advantages and the like, which are specified below regarding only one aspect of the invention for the purposes of avoiding repetition, apply correspondingly with reference to the remaining aspects of the invention.

Having said this, the present invention is described in more detail below.

The dispenser according to the invention comprises a piston actuator which is releasably connectable to the piston of the piston-cylinder unit in such a manner that the piston is movable for taking up and/or dispensing fluid volumes by means of the piston actuator.

A basic concept of the present invention consists in combining incremental distance measuring of a relative movement between the piston and the cylinder with determining the position of the piston actuator by a position element which is motionally coupled with the piston actuator. The dispenser according to the present invention thus comprises a position determining device which has a first position element and a second position element. The first position element is arranged rigidly in or on the housing of the dispenser and the second position element is motionally coupled with the piston actuator. The position determining device is constructed to, in particular continuously, determine the position of the second position element.

As a result of the motional coupling of the second position element with the piston actuator and the connection between the piston actuator and the piston of a piston-cylinder unit attached to the dispenser, the position determining device can determine the position of the piston directly and without any mechanical play.

The dispenser according to the invention can provide the position of the piston or piston actuator immediately after switching on the power supply, preferably updated continuously. Referencing is not necessary. The determined positions can be called up at any time for further functions of the dispenser.

The dispenser according to the invention can determine, for example, how far the piston is inserted into the cylinder of the piston-cylinder unit. Should the dispenser according to the invention ascertain, for example, that the piston is not inserted fully into the cylinder of the piston-cylinder unit, the dispenser can insert the piston into the cylinder fully by means of the piston actuator in order to generate a defined starting position, for example for taking up a fluid volume and/or determining incrementally—by means of the incremental distance measuring device—the distance traveled by the piston relative to the housing of the dispenser when there is a relative movement between the piston and the cylinder.

Using the dispenser according to the invention it is also possible to ascertain whether the position of the piston or piston actuator has changed with the dispenser in a disconnected state.

The dispenser according to the invention enables, in addition, the incremental distance measuring device and/or the position determining device to be adjusted. If a reference position of the piston or of the piston actuator is known to the dispenser, the dispenser can thus determine an end or intermediate position proceeding from said reference position by way of a distance of the piston, determined by the incremental distance measuring device, relative to the housing of the dispenser when there is a relative movement between the piston and the cylinder and can compare said end or intermediate position with the position value of the position determining device. If the position values do not match, the dispenser can perform an adjustment.

It is also helpful when the second position element is arranged at a known distance from a reference point of the piston.

Finally, the dispenser according to the invention enables a continuously possible plausibility check on the values of the incremental distance measuring device and of the position determining device.

The dispenser according to the invention therefore also enables precise taking up and dispensing of fluid volumes, in particular with a high degree of correctness and a low variation coefficient.

In the case of a first preferred embodiment of the dispenser according to the invention, the first position element is a position sensor and the second position element is a position marker. The position sensor is constructed to, in particular continuously, determine the position of the position marker.

The position sensor preferably comprises a printed circuit board and/or the position marker preferably comprises an electrical resonator, in a preferred manner having a coil and/or a capacitor.

In the case of a second preferred embodiment of the dispenser according to the invention, the first position element is a position indicator, preferably with at least one measuring body, in particular two rulers, and the second position element is a position sensor with at least one, in particular optical, sensor. The position sensor is constructed to, in particular continuously, determine its position, preferably to read its position from the position indicator.

The following preferred designs refer to both preferred embodiments.

The position determining device is preferably constructed for the optical, inductive and/or capacitive, preferably resonantly inductive, determination of the position of the second position element. In this case, it is preferred when there is no mechanical or electrical contact between the first position element and the second position element. This enables the piston actuator to move in an unobstructed manner in the housing of the dispenser.

It has proved advantageous when the incremental distance measuring device comprises a rotary measuring device, by means of which the revolutions of a motor of the dispenser that drives the piston actuator are determinable and consequently the distance travelled by the piston when the piston actuator is displaced is incrementally determinable. Here, the incremental distance measuring device is set up therefore for indirect distance measuring by means of the revolutions of the motor as an auxiliary variable.

The position determining device is constructed in a preferred manner to determine the distance traveled by the piston relative to the first position element and/or to the housing of the dispenser during a relative movement between the piston and the cylinder. This can be effected, for example, by subtracting two position values of the position determining device. Consequently, absolute distance measuring is effected here so to speak by means of the position determining device. This enables, among other things, adjustment of the distance measurements of both devices and a plausibility check on the values of both devices.

The incremental distance measuring device preferably has a smaller resolution with regard to measuring the distance than the position determining device (absolute distance measuring).

It is preferred when the dispenser is constructed to determine a variable reversal stroke on the basis of a subtraction between measured values of the incremental distance measuring device and of the position determining device. As an alternative to this or in addition to it, the dispenser can be constructed to determine a starting point, which is defined according to a variable reversal stroke, on the basis of a measured value of the position determining device.

A reversal stroke is to be understood here as the distance traveled by the piston actuator during the transition from the taking-up of a fluid volume to the dispensing of a fluid volume or the other way around. It is explained, among other things, by play and flexible deformation in the drive train of the motor that drives the piston actuator. It depends, for example, on the size and accompanying mechanical resistance of the piston-cylinder unit attached to the dispenser.

A static reversal stroke is set mostly with generic dosing devices. A static reversal stroke reduces the possible usable piston stroke and frequently leads to imprecise taking up and/or dispensing of fluid volumes.

The dispenser according to the invention can determine a variable reversal stroke, for example, as a result of comparing an incremental distance measurement (revolutions of the motor) and an absolute distance measurement (piston movement between two position positions). The piston stroke can consequently be better utilized and the accuracy increased.

If a starting point has been determined after a variable reversal point by means of an absolute distance measurement of the position determining device, a previously taken up fluid volume can be dispensed from the starting point or the incremental distance measuring of the piston actuator is commenced with the take-up of a fluid volume.

The piston actuator is preferably movable toward the piston, in particular a piston head of the piston, until a stop of the piston actuator abuts against an end face of the piston. Said movement, which is also designated as a blocking movement, serves for determining a piston-side reference point. The absolute position of said piston-side reference point can be determined by means of the position determining device.

The dispenser advantageously comprises an acquisition element which is introducible in the axial direction at least in part into an axially aligned recess, in particular groove, in the end face of the piston. The second position element or the position marker is motionally coupled with the acquisition element. The depth of the recess is determinable by means of the position determining device.

The axially aligned recess provides an information carrier portion. The depth of the recess specifies the type of piston-cylinder unit at least in part. In this case, the term "type" designates, for example, a purpose, a state and/or a property of the piston-cylinder unit, such as, for example, the maximum fluid volumes that can be taken up and/or dispensed.

The expression "axially aligned recess" is to be understood, in this case, such that said recess is accessible in the axial direction of the piston-cylinder unit and/or the information thereof can be determined in the axial direction of the piston-cylinder unit. The axially aligned recess has a geometric extent in the axial direction, by means of which axial extent the determinable information is coded. In addition, the axially aligned recess has a geometric extent in the radial direction and in the circumferential direction. The axially aligned recess can be realized as a groove, that is to say not completely surrounded by piston material. Such a design makes cleaning the recess easier and provides a simple control option.

The piston-side reference point marks, in particular, the starting point of determining the depth of the axially aligned recess of the piston.

The acquisition element is preferably realized a in a plunger-shaped and/or pin-shaped manner and/or is spring-loaded, in particular is prestressed elastically in opposition to the insertion direction of the piston-cylinder unit. It is particularly preferred when the dispenser comprises a locking element, by way of which the acquisition element can be moved into a release position and held or locked there. As soon as the locking element no longer blocks the acquisition element, the spring-loaded acquisition element is moved toward the piston and finally is pressed into the recess of the piston which extends in the axial direction.

The dispenser preferably has means, in particular a light barrier, for the mechanical, electronic, inductive and/or optical identification of the attaching of the piston-cylinder unit to the dispenser.

In a preferred manner, the dispenser according to the invention is a fully autonomous, hand-held and motor-driven device which combines all the components in a housing independent of the location. Said components include, as usual, a drive, preferably a motor drive, a gear unit which converts the rotational movement of the motor into a longitudinal movement of the piston actuator, electronics, a power supply and naturally a coupling device for connecting the piston of the piston-cylinder unit to the piston actuator.

According to a second aspect of the invention, the previously depicted object set is achieved by a system for taking up and dispensing fluid volumes according to claim 15.

The system according to the second aspect of the invention comprises a piston-cylinder unit, which is realized as an exchangeable part, and a dispenser which is as described previously. The piston-cylinder unit is releasably attached to the dispenser and comprises a piston and a cylinder which is fixed on the dispenser. The dispenser has a piston actuator which is releasably connected to the piston in such a manner that the piston is movable by means of the piston actuator for taking up and/or dispensing fluid volumes.

The previously indicated object set is also achieved by a method for taking up and dispensing fluid volumes, as is explained below.

The method serves for taking up and dispensing adjustable fluid volumes by means of a dispenser, to which a piston-cylinder unit, which is realized as an exchangeable part, is releasably attachable. The piston-cylinder unit comprises a piston and a cylinder. The dispenser comprises a housing and a piston actuator. In particular, the dispenser is realized as described further above.

The method includes the following method steps:
a) releasably attaching the piston-cylinder unit to the dispenser, preferably by means of a movement which extends at least substantially in the axial direction of the dispenser;
b) generating a relative movement between the piston and the cylinder by means of the piston actuator;
c) incrementally determining the distance traveled by the piston relative to the housing of the dispenser; and
d) determining the absolute travel position of a position element of the dispenser which is motionally coupled with the piston actuator.

In step a) of the method, the piston of the piston-cylinder unit is advantageously releasably connected to the piston actuator of the dispenser at a fastening portion of the piston. A coupling between the piston actuator and the piston is achieved in this way.

The cylinder of the piston-cylinder unit is preferably fixed to the dispenser in step a).

It is preferred when the completion of a successful attachment of the piston-cylinder unit to the dispenser is detected mechanically, electronically, inductively and/or optically, preferably by means of a light barrier.

In the case of a preferred embodiment of the method, in step c) the revolutions of a motor of the dispenser, which drives the piston actuator, are determined by means of a rotary measuring device of the dispenser. Consequently, the distance traveled by the piston is incrementally determined while the piston actuator is moved by the motor.

The absolute travel position of the position element is preferably continuously determined.

A reversal in the direction of the relative movement between the piston and the cylinder is advantageously determined by way of determined positions of the position element. A starting point for the determination of a further relative movement can be determined.

In a preferred manner, at least one incrementally determined distance traveled by the piston is related to at least one determined position of the position element. On this basis, a variable reversal stroke can be determined and/or the relative movement between the piston and the cylinder determined, an adjusting of the distance determining and/or the position determining can be performed and/or plausibility checks can be carried out with regard to the determined distances and/or the determined positions.

In the case of a preferred embodiment of the method, a piston-side reference point is determined by the piston actuator of the dispenser being moved toward the piston until a stop of the piston actuator abuts against an end face of the piston. In this case, the distance traveled by the piston actuator can be determined, in particular by means of the incremental distance measuring device.

A acquisition element of the dispenser is preferably inserted in the axial direction at least in part into an axially aligned recess in an end face of the piston and the depth of said recess is determined by way of determined positions of the second position element or position marker. The determined depth value can be used to identify the type of the piston-cylinder unit.

The invention is explained in more detail below by way of the description of preferred exemplary embodiments, partly with reference to the drawings. The features described above and/or in the following description can be combined with one another, where needed, but can also be realized independently from one another, even if this is not described explicitly in detail.

DETAILED DESCRIPTION OF THE INVENTION

Figure 1:
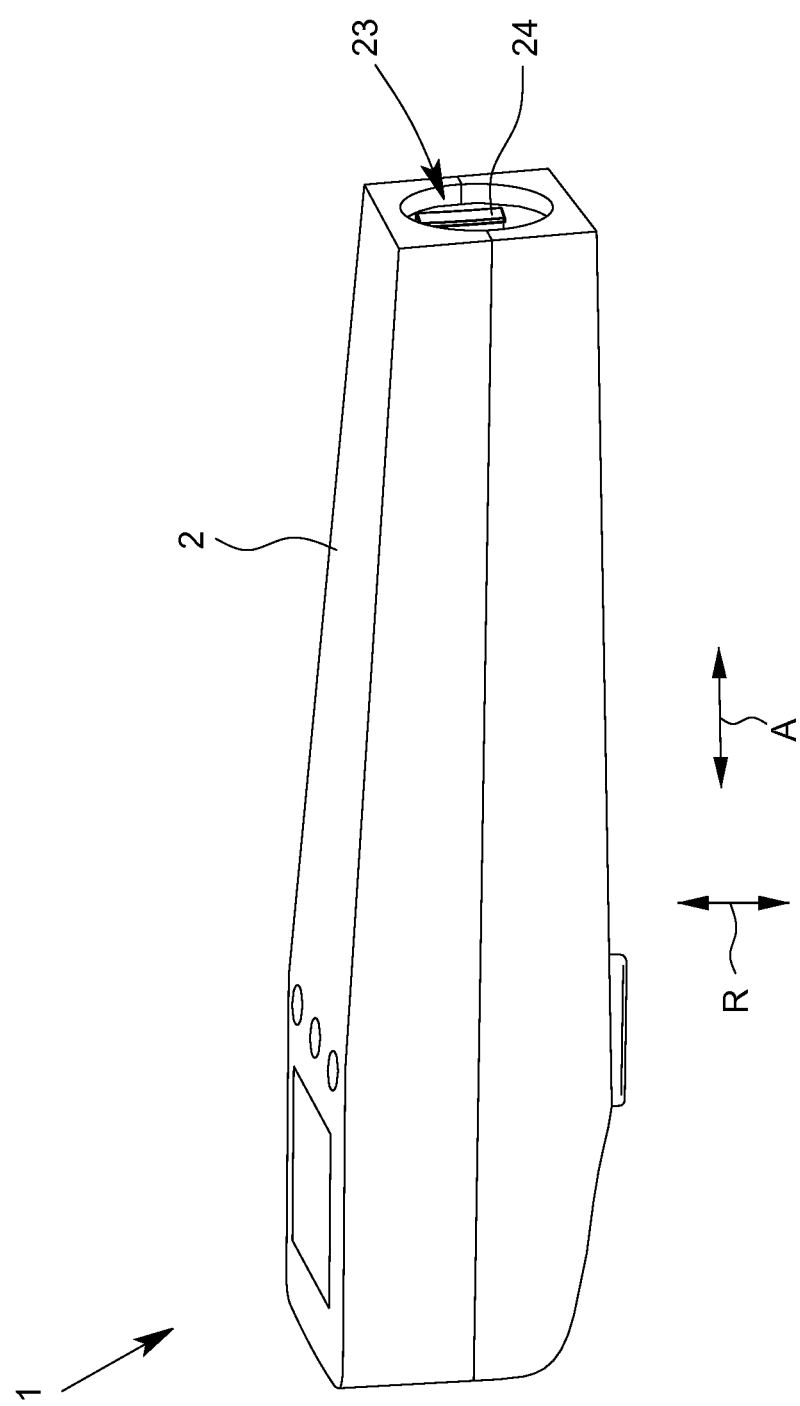
FIG. 1 is a schematic perspective view of a preferred embodiment of a dispenser according to the invention.

FIG. 1 shows a schematic representation of a perspective view of a preferred embodiment of a dispenser 1 according to the invention for taking up and dispensing fluid volumes. The dispenser 1 has a housing 2 with an opening 23 and a fixing device 24 for the piston-cylinder unit 3 which is arranged behind the opening 23 inside the housing 2.

Figure 2:
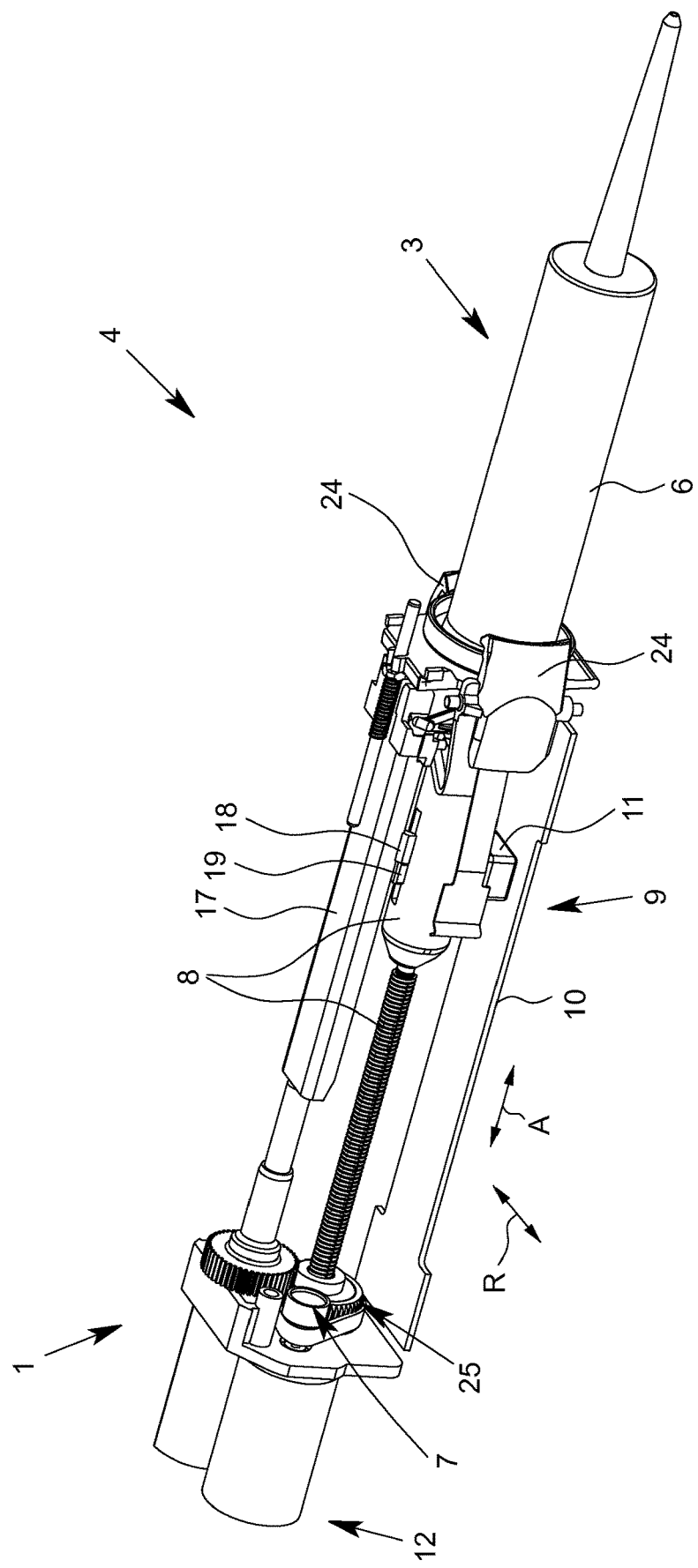
FIG. 2 is a simplified schematic perspective view of a preferred embodiment of a system according to the invention with the dispenser of FIG. 1 and a piston-cylinder unit inserted into the dispenser, leaving out parts of the dispenser.

FIG. 2 shows a schematic representation of a perspective view of the dispenser 1 from FIG. 1 and of a piston-cylinder unit 3, which is inserted into the dispenser 1 and held by the fixing device 24, as parts of a preferred embodiment of a system 4 according to the invention for taking up and dispensing fluid volumes. In this case, the dispenser 1 is only shown in part. FIG. 2 is restricted to showing the components which are necessary to explaining the present invention.

Figure 3:
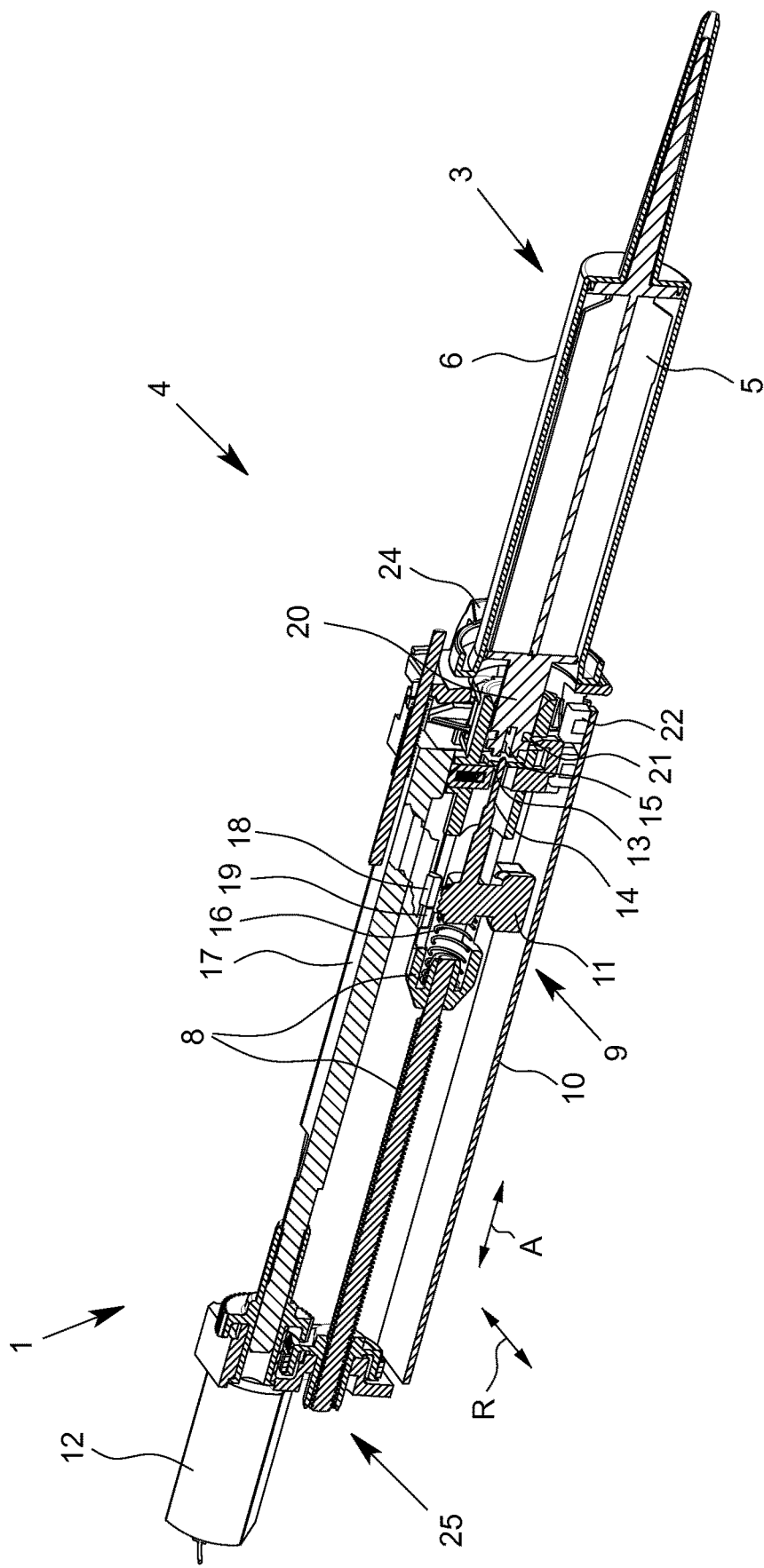
FIG. 3 is a perspective view of a longitudinal section through the system of FIG. 2.

FIG. 3 shows a schematic representation of a perspective view of a longitudinal section through the system 4 of FIG. 2.

The dispenser 1 and the piston-cylinder unit 3 have an axial direction A shown in FIG. 2 and a radial direction R which extends perpendicularly to the axial direction A and through the longitudinal axis of the dispenser 1 or of the piston-cylinder unit 3.

The piston-cylinder unit 3 is an exchangeable part. It can be realized in the form of a syringe and can be present in various sizes with different volumetric capacities. It comprises a sealed piston 5 which is movable in a cylinder 6 of the piston-cylinder unit 3 for the purpose of taking up or drawing in and dispensing or ejecting a liquid which is to be pipetted or dosed. The piston 5 can only be seen in FIG. 3.

With the piston-cylinder unit 3 in the inserted state, the cylinder 6 abuts against a rocker (not shown) of the dispenser 1. Hereby and with the aid of the fixing device 24, the cylinder 6 is fixed on the dispenser 1 or on the system 4 so that, with regard to the piston-cylinder unit 3, only the piston 5 is movable in the cylinder 6 for taking up or drawing in or dispensing or ejecting liquid.

The dispenser 1 has an incremental distance measuring device 7 which is constructed such that, in the case of a relative movement between the piston 5 and the cylinder 6, the distance traveled by the piston 5 relative to the housing 2 of the dispenser 1 can be incrementally determined.

The dispenser 1 or the system 4 comprises a piston actuator 8 which is releasably connectable to the piston 5 of the piston-cylinder unit 3 in such a manner that the piston 5 is movable by means of the piston actuator 8 to take up and/or dispense fluid volumes.

The dispenser 1 or the system 4 comprises a position determining device 9 which has a first position element 10 and a second position element 11. The first position element 10 is arranged rigidly in or on the housing 2 of the dispenser 1. The second position element 11 is motionally coupled with the piston actuator 8, by the second position element 11 being arranged on the piston actuator 8. The position determining device 9 is constructed to determine the position of the second position element 11.

In the case of the embodiment that is shown and preferred, the dispenser 1 can provide the respective position of the second position element 11 immediately after the power supply is switched on. The respective position is continuously determined and can be called up at any time by further electronics of the dispenser 1.

In the case of the embodiment that is shown and preferred, the first position element 10 is a position sensor and the second position element 11 a position marker. The position sensor 10 is constructed to determine the position of the position marker 11.

The position determining device 9 is constructed here to determine the position of the position marker 11 in a resonantly inductive manner. There is no mechanical and electrical contact between the position sensor 10 and the position marker 11.

The position sensor 10 here comprises a printed circuit board. The position marker 11 has an electrical resonator with multiple coils and a capacitor. In this case, one of the coils is used to provide the resonator with power. The coils are arranged such that a sine/cosine variation in the coupling factor is generated when the position marker 11 is moved. The calculation of the respective position of the position marker 11 corresponds to the calculation of a phase angle and is carried out by way of an inverse four quadrant tangent.

The position determining device 9 enables the position of the position marker 11 to be determined in a simple, sturdy and cost-efficient manner.

In the case of the embodiment that is shown and preferred, the piston actuator 8 is driven by a motor 12 via a gear unit 25 which is disclosed in the prior art. The incremental distance measuring device 7 comprises a rotary measuring device by means of which the revolutions of the motor 12 of the dispenser 1 can be determined. The distance traveled by the piston 5 when the piston actuator 8 is displaced can be determined incrementally based on the revolutions determined and on a conversion factor of the gear unit 25.

In the case of the embodiment that is shown and preferred, the position determining device 9 is constructed to determine the distance traveled by the piston 5 relative to the position sensor 10 and to the housing 2 in the case of a relative movement between the piston 5 and the cylinder 6. In particular, the position determining device 9 is constructed to subtract two determined position values. Consequently, the position determining device 9 can perform an absolute distance measurement. In this case, the incremental distance measuring device 7 has a smaller resolution with regard to the distance measurement than the position determining device 9.

In the case of the embodiment that is shown and preferred, the dispenser 1 is constructed to determine a variable reversal stroke based on a subtraction between measured values of the incremental distance measuring device 7 and of the position determining device 9. In addition, the dispenser 1 is constructed to determine a starting point which is defined after a variable reversal stroke based on a measured value of the position determining device 9. A fluid volume previously taken up can be dispensed from the starting point determined in this way or the incremental distance measurement of the piston actuator 8 is commenced in each case when a fluid volume is taken up.

In the case of the embodiment that is shown and preferred, the piston actuator 8 can be moved toward the piston 5 for determining a piston-side reference point until a stop 13 of the piston actuator 8 abuts against an end face of the piston 5. The absolute position of said piston-side reference point can be determined by means of the position determining device 9 and/or by means of the incremental distance measuring device 7.

In the case of the embodiment that is shown and preferred, the dispenser 1 comprises an acquisition element 14 which is insertable in the axial direction A at least in part into an axially aligned recess 15 in an end face of the piston 5. The position marker 11 is motionally coupled with the acquisition element 14. The depth of the recess 15 can be determined by means of the position determining device 9. Based on the depth of the recess 15 determined in this manner, it is possible to identify at least in part the type of the piston-cylinder unit 3 with its individual dimensions and requirements when used with the dispenser 1.

The previously determined piston-side reference point marks the starting point of determining the depth of the recess 15.

The acquisition element 14 is prestressed elastically here in opposition to the insertion direction of the piston-cylinder unit 3 by means of a spring 16. The dispenser 1 comprises a locking element 17, by way of which the acquisition element 14 can be moved into a release position and be held there. The locking element 17 holds the acquisition element 14 in the release position by an entrainment means 18 of the locking element 17 counteracting the force of the spring 16 at a continuation 19 of the acquisition element 14 and blocking a movement of the acquisition element 14 in the direction of the spring force (that is to say in the axial direction A toward the piston-cylinder unit 3).

The locking element 17 can be displaced in the axial direction A in the dispenser 1 and relative to the housing 2 and to the piston actuator 8. As a result of displacing the locking element 17 in the direction of the piston-cylinder unit 3, movement of the acquisition element 14 is no longer blocked so that the acquisition element 14 is pressed by the spring 16 toward the piston 5 and then into the axially aligned recess 15 until the acquisition element 14 contacts the end of the recess 15 and is blocked there.

The axially aligned recess 15 is upwardly open here in the axial direction A, open to the left, therefore, in FIG. 3. The recess 15 is realized here in the form of a groove. It is therefore not a bore which is surrounded in the radial direction R. The recess is, in fact, outwardly open in part in the radial direction R, along the entire depth of the recess 15. As an alternative to this, the axially aligned recess 15 can be realized as a blind hole.

In the case of the embodiment that is shown and preferred, the depth of the axially aligned recess 15 can assume one of multiple discrete values, for example one of eight possible depth values. The discrete depth values comprise a minimum distance, preferably approximately 2 mm. If a depth is 0 mm, it is not a recess in the sense of the present invention.

In the case of the embodiment that is shown and preferred, the piston 5, in particular a piston head 20 of the piston 5, has an information carrier portion 21 which specifies in part the type of the piston-cylinder unit 3 and is aligned radially. In this case, the radially aligned information carrier portion 21 is formed by a recess 21 on the piston head 20, which recess extends in the radial direction R and extends in the circumferential direction of the piston-cylinder unit 3. It can be seen in FIG. 3 that the radially aligned recess 21 is formed as a result of the piston head 20 having a smaller diameter in said portion.

In the case of the embodiment that is shown and preferred, the depth of the axially aligned recess 15 and the depth of the radially aligned recess 21 specify the type of the piston-cylinder unit 3.

In the case of the embodiment that is shown and preferred, the dispenser 1 has a sensor device for detecting the attachment of the piston-cylinder unit 3 to the dispenser 1. A light barrier 22 is provided here as a sensor device. Once successful attachment of a piston-cylinder unit 3 has been detected, fluids can be taken up into the cylinder 6 or dispensed from the cylinder 6.

The dispenser 1 has further devices which are not shown, among others an electronic control device, a gear unit, power supply equipment, a coupling device for connecting the piston 5 to the piston actuator 8, a display device and an input device.

A preferred sequence of a method for picking up and dispensing fluid volumes is depicted below.

First of all, the piston-cylinder unit 3 is inserted releasably into the dispenser 1 by means of a movement which extends at least substantially in the axial direction A. The cylinder 6 of the piston-cylinder unit 3 is fixed.

Once the piston-cylinder unit 3 has been inserted successfully into the dispenser 1, this is detected by means of the sensor device, here the light barrier 22.

The piston-side reference point is then determined by generating a relative movement between the piston 5 and the piston actuator 8. In this case, the piston actuator 8 is moved toward the piston 5 until the stop 13 of the piston actuator 8 abuts against an end face of the piston 5 (blocked movement). The length of the relative movement is determined by means of the incremental distance measuring device 7 or the position determining device 9.

The piston-side reference point is then determined as absolute travel position by means of the position determining device 9, which is motionally coupled with the piston actuator 8. The reference point provides, as it were, a distance calibration which makes the method at least largely independent of differences in the dimensional tolerances of the parts of the piston-cylinder unit 3. For the determining of the reference point enables a starting point to be established for reading-out the information of the recesses 15, 21.

In the case of the preferred embodiment of the method, after the blocked movement, the acquisition element 14 of the dispensers 1 is inserted in the axial direction A at least in part into the axially aligned recess 15 and the depth of said recess 15 is determined by way of determined positions of the position marker 11. The determined depth value is used to identify in part the type of the piston-cylinder unit 3.

Thereafter, at the same time or prior to this, the piston head 20 of the piston-cylinder unit 3 is connected releasably to the piston actuator 8 of the dispenser 1. A coupling between the piston actuator 8 and the piston 5 is achieved in this way.

A relative movement between the piston 5 and the cylinder 6 is then generated by the piston actuator 8 moving the piston 5, in particular displacing it in a linear manner. In this case, the piston actuator 8 is driven by the motor 12. The distance traveled by the piston actuator 8 in the case of said relative movement corresponds to the distance traveled in this case by the piston 5.

The distance traveled by the piston 5 in the case of said relative movement relative to the housing 2 of the dispenser 1 is determined incrementally by means of the incremental distance measuring device 7. In this case, the revolutions of the motor 12 which drives the piston actuator 8 are determined.

In addition, the absolute travel position of the position marker 11 of the dispenser 1 is determined continuously by means of the position determining device 9. Absolute distances are calculated as a result of subtracting two absolute travel positions.

If a reversal of direction takes place, for example, when changing from taking up to dispensing a fluid volume or the other way around, during the relative movement between the piston 5 and the cylinder 6, said reversal of direction is determined immediately at the piston actuator 8 and at the piston 5 coupled therewith by way of the continuous determining of the absolute travel positions of the position marker 11. The stroke of the driving motor 12 when the direction is reversed, without the piston actuator 8 being moved and a relative movement being generated between the piston 5 and cylinder 6, is variable as a result of different driving forces, mechanical play and wear. Both the reversal stroke and the relative movement can be independently determined. In addition, a starting point is determined for determining a further relative movement after the direction has been reversed. From the starting point determined in this way, the distance traveled by the piston 5 relative to the housing 2 is determined incrementally by means of the incremental distance measuring device 7.

In the case of the preferred embodiment of the method according to the invention, the values of incremental distance measurements are related to determined positions of the position marker 11, in particular absolute distance measurements by way of the determined positions of the position marker 11. The distance measurement and the position determination are adjusted on this basis. In addition, the related values are compared to one another and any deviations are used for adjustment. In this way, plausibility checks are also carried out with regard to the determined distances and to the determined positions. Non-plausible values, for example, can be rejected.

What is claimed is:

1. A dispenser for taking up and dispensing fluid volumes, comprising:
    a housing,
    an exchangeable piston-cylinder unit having a piston and a cylinder and being releasably attached to the housing,
    a piston actuator which is moveable in the housing and is releasably connected to said piston in such a manner that said piston is moved translationally by the piston actuator for taking up and dispensing fluid volumes,
    an incremental distance measuring device in the housing and configured to incrementally determine a distance axially traveled by said piston of said piston-cylinder unit relative to said housing, and
    a position determining device which has a first position element and a second position element,
    wherein the first position element is arranged rigidly fixed in or on said housing and the second position element is coupled to axially move with the piston actuator, and
    wherein the position determining device determines the axial position of the second position element.

2. The dispenser as claimed in claim 1, wherein the first position element is a position sensor and the second position element is a position marker, and wherein the position sensor is operative to determine the position of the position marker.

3. The dispenser as claimed in claim 2, wherein the position sensor comprises a printed circuit board.

4. The dispenser as claimed in claim 2, wherein the position marker comprises an electrical resonator.

5. The dispenser as claimed in claim 4, wherein the electrical resonator comprises at least one of a coil or a capacitor.

6. The dispenser as claimed in claim 1, wherein the first position element is a position indicator and the second position element is a position sensor, and wherein the position sensor is constructed to determine the position at which the position sensor is located using the position indicator.

7. The dispenser as claimed in claim 1, wherein the position determining device is constructed without electrical contact between the first position element and the second position element.

8. The dispenser as claimed in claim 1, further comprising a motor coupled to the piston actuator and configured to perform revolutions to drive the piston actuator and wherein the incremental distance measuring device comprises a rotary measuring device for determining the number of revolutions of the motor and thus for incrementally determining the distance traveled by the piston during displacement by the piston actuator.

9. The dispenser as claimed in claim 1, wherein the position determining device is constructed to determine the distance traveled by the piston relative to at least one of the first position element or to said housing during a relative movement between the piston and the cylinder of said piston-cylinder unit.

10. The dispenser as claimed in claim 2, further comprising an acquisition element in the housing, wherein the acquisition element is insertable into a recess in an end face of the piston, and wherein the second position element or the position marker is coupled to move with the acquisition element, and wherein a depth of the recess is determinable by the position determining device.

\* \* \* \* \*